(12) United States Patent
Houle et al.

(10) Patent No.: US 8,211,024 B2
(45) Date of Patent: Jul. 3, 2012

(54) MEDICAL ULTRASOUND PRESSURE GRADIENT MEASUREMENT

(75) Inventors: Helene C. Houle, Sunnyvale, CA (US);
Liexiang Fan, Issaquah, WA (US);
Matthew Holladay, Britton, MI (US);
King Yuen Wong, Issaquah, WA (US);
Wayne J. Gueck, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1163 days.

(21) Appl. No.: 11/147,098

(22) Filed: Jun. 6, 2005

(65) Prior Publication Data

US 2007/0016037 A1 Jan. 18, 2007

(51) Int. Cl.
*A61B 8/14* (2006.01)
(52) U.S. Cl. ...................................................... 600/459
(58) Field of Classification Search ........... 600/437–466
See application file for complete search history.

(56) References Cited

U.S. PATENT DOCUMENTS

| | | | |
|---|---|---|---|
| 4,796,634 A * | 1/1989 | Huntsman et al. ............ | 600/457 |
| 5,226,420 A | 7/1993 | Peterson | |
| 5,615,680 A * | 4/1997 | Sano ............................. | 600/437 |
| RE35,720 E * | 2/1998 | Arenson et al. ............... | 600/441 |
| 5,784,026 A | 7/1998 | Smith et al. | |
| 6,110,117 A | 8/2000 | Ji et al. | |
| 6,149,595 A * | 11/2000 | Seitz et al. ..................... | 600/438 |
| 6,241,675 B1 * | 6/2001 | Smith et al. ................... | 600/443 |
| 6,379,303 B1 * | 4/2002 | Seitz et al. ..................... | 600/438 |
| 6,565,513 B1 * | 5/2003 | Phillips ......................... | 600/454 |
| 6,599,248 B1 * | 7/2003 | Tamura ......................... | 600/454 |
| 6,682,485 B2 * | 1/2004 | Seitz et al. ..................... | 600/438 |
| 7,547,283 B2 * | 6/2009 | Mourad et al. ................ | 600/459 |
| 2004/0088123 A1 * | 5/2004 | Ji ................................... | 702/45 |
| 2005/0015009 A1 * | 1/2005 | Mourad et al. ................ | 600/438 |
| 2006/0079782 A1 * | 4/2006 | Beach et al. .................. | 600/450 |
| 2007/0016072 A1 * | 1/2007 | Grunwald et al. ............ | 600/468 |
| 2007/0016084 A1 * | 1/2007 | Denault ......................... | 600/485 |

OTHER PUBLICATIONS

Noninvasive Estimation of Transmitral Pressure Drop Across the Normal Mitral Valve in Humans: Importance of Convective and Inertial Forces During Left Ventricular Filing; Michael S. Firstenberg, M.D. et al.; Journal of American College of Cardiology; vol. 36, No. 6, 2000; pp. 1942-1949.

* cited by examiner

*Primary Examiner* — Sanjay Cattungal

(57) ABSTRACT

Flow information (e.g., velocity and acceleration) and/or pressure gradient information are determined with ultrasound. Both velocity and acceleration are simultaneously estimated using a model and least squares analysis. Antialiasing of velocity information may be provided using the model and least squares analysis. Pressure gradient is calculated from velocity information automatically, more likely providing consistent measurements. Consistency may be increased further by automatically positioning a region of interest in either a multidimensional spatial image or a spatial-temporal image. A parametric image of pressure gradient for each spatial location within the image is generated as well as a delta pressure curve. Any single one or combinations of two or more of the features described above may be used.

17 Claims, 2 Drawing Sheets

MEDICAL ULTRASOUND PRESSURE GRADIENT MEASUREMENT

BACKGROUND

This present invention relates to using velocity information. In particular, medical ultrasound is used to generate velocity information and/or related pressure gradient measurements.

Medical diagnostic ultrasound systems generate velocity information by Doppler processing. In the color Doppler technique for estimating velocity, an ensemble of transmissions and corresponding receptions to the same locations, such as 8 to 16 pulses along a scan line, are correlated to identify a phase shift. The ensemble size is large in order to achieve good signal-to-noise ratio and detection sensitivity. Large ensemble size in general results in low flow frame rate. Persistence is used to avoid flash artifacts. However, the persistence algorithm in general is not a good strategy in terms of temporal filtering the noise of the estimated flow. The ensemble occurs within a short time period such that the phase shift between adjacent pulses is likely constant. A velocity is estimated from the phase shift. An acceleration is then determined from a plurality of velocity estimates.

The velocity information may be used to identify pressure gradients. Pressure gradient in intraventricular regions and transmittal pressure drop have significant diagnosis implications for the assessment of ventricular load. Ultrasound Doppler measurement provides the velocity of blood flow, enabling the potential to estimate the pressure gradient. Pressure gradient is estimated using Euler's equation (i.e., the pressure gradient is proportional to the sum of the temporal velocity derivative and the velocity multiplied spatial derivative of velocity). A workstation was used after previously acquiring ultrasound color M-mode data. A color M-mode image provides a spatial-temporal velocity distribution along a scan line. By positioning the scan line along the inflow tract across the mitral valve and into the left ventricle throughout diastole, intraventricular pressure gradient may be estimated or indicated by processing velocity information.

Alternatively, a difference in velocity is calculated using a caliper function on a color M-mode image. Rather than using the pressure gradient, the left ventricular diastolic function may be assessed with measurements of the inflow velocities at the mitral valve. In yet another alternative, a high-fidelity pressure catheter read-out provides pressure gradient. Simultaneous volume measurements with the pressure gradient information are used to reconstruct pressure-volume loops. However, the use of a catheter is invasive and uses tedious tracing of ventricular contours.

BRIEF SUMMARY

By way of introduction, the preferred embodiments described below include a methods and systems for determining flow information (e.g., velocity and acceleration) and/or measuring pressure gradient with ultrasound. Both velocity and acceleration are simultaneously estimated using a model and least squares analysis. Anti-aliasing of velocity information may be provided using the model and least squares analysis. Pressure gradient is calculated from velocity information automatically, more likely providing consistent measurements. Consistency may be increased further by automatically positioning a region of interest in either a multidimensional spatial image or a spatial-temporal image. A parametric image of pressure gradient for each spatial location within the image is generated. Any single one or combinations of two or more of the features described above may be used.

In a first aspect, a method is provided for measuring pressure gradient with ultrasound. An ultrasound system scans a patient. In real time with the scanning, the ultrasound system automatically computes a pressure gradient as a function of ultrasound data responsive to the scanning.

In a second aspect, a method is provided for measuring pressure gradient with ultrasound. A region of interest is automatically detected. A pressure gradient is automatically computed as a function of ultrasound data within the region of interest.

In a third aspect, an ultrasound system is provided for measuring pressure gradient with ultrasound. A beamformer generates ultrasound data. A processor connects with the beamformer. The processor automatically computes, as ultrasound data is generated, a pressure gradient as a function of the ultrasound data.

In a fourth aspect, a method is provided for determining flow information with ultrasound. Ultrasound information is acquired. Velocity and acceleration are simultaneously determining from the ultrasound information.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The detailed description includes two sections—pressure gradient and flow estimation. The processes of each section may be used independently or in combination. For example, pressure gradient is measured using velocity values with or without anti-aliasing estimated as discussed below or using other methods. As another example, flow is estimated with or without anti-aliasing described below for uses other than pressure gradient measurement.

Pressure Gradient

Figure 1:
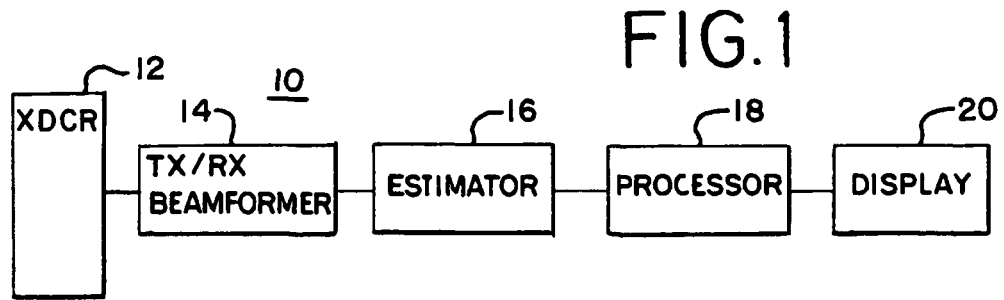
FIG. 1 is a block diagram of one embodiment of a system for estimating velocity and/or measuring pressure gradient.

FIG. 1 shows an ultrasound system 10 for measuring pressure gradient with ultrasound. The system 10 includes a transducer 12, a beamformer 14, an estimator 16, a processor 18 and a display 20. Additional, different or fewer components may be provided. For example, a scan converter converts estimated data prior to the processor 18 and/or the display 20. The ultrasound system 10 is a medical diagnostic ultrasound system for real-time scanning. Alternatively, the system 10 is free of the transducer 12 and beamformer 14 and is a workstation or computer remote from a location of scanning.

The transducer 12 is a single element, one dimensional array, or multi-dimensional array. The transducer 12 is a piezoelectric or microelectromechanical material for transducing between acoustic and electric energies. Using either electric, mechanical or both electric and mechanical steering, the transducer 12 transmits and receives along one or more scan lines for scanning a patient with acoustic energy.

The beamformer 14 is a transmit, receive or both transmit and receiver beamformer for generating ultrasound data. As a transmit beamformer, the beamformer 14 includes pulsars or waveform generators for generating transmit waveforms for each element of the transducer 12. Using waveform timing, delays or phase rotators, the waveforms are relatively delayed for electronic steering. Amplifiers, digital-to-analog converters and/or source voltage variation may provide relative apodization for the waveforms of each element. As a receive beamformer, delays and/or phase rotators relatively delay signals from each element. Apodization may be provided by amplifiers and/or analog-to-digital converters. The received signals from the different elements from one or more transmits are then summed by one or more summers for each of a plurality of image locations. Filters and/or a transmit-receive switch may also be provided for the transmit or receive beamformers. Conventional beamformers or unconventional (e.g., plane wave) beamformers as in U.S. Pat. Nos. 6,309,356, 6,517,489, and 6,551,246 may be used.

Transmit and receive sequence of pulses implemented by the beamformer 14 are the same or different depending on the imaging mode. For example, a repetitive sequence of pulses is transmitted along a same scan line to generate M-mode data. For intensity M-mode data, each receive beam along the scan line is used to determine intensities. For color M-mode data, an ensemble of pulses (transmit and receive beams) are used along the scan line. The ensemble includes 2-20 pulses used to estimate flow characteristics, such as velocity. The ensemble is repeated for further estimations. For two or three dimensional flow information, the ensemble is repeated for each of a plurality of different scan lines.

In one embodiment, the beamformer 14 implements plane wave imaging. A plane wave is transmitted. Receive beams are formed for a plurality of scan lines in response to each plane wave. For imaging flow, a plurality of plane wave transmissions may be used.

The estimator 16 is an intensity, velocity, power, turbulence and/or other now known or later developed detector. For example, the estimator 16 includes a B-mode detector for B or M mode intensity imaging and a Doppler detector for color or flow imaging. The Doppler detector estimates velocity from phase shifts using correlation or the simultaneous estimation discussed below. The estimator 16 optionally includes an anti-alias filter, such as a processor based filtering.

The processor is a control processor, digital signal processor, general processor, field programmably gate array, application specific integrated circuit, analog circuit, digital circuit or combinations thereof. The processor 18 is part of the system 10 and connects with the beamformer 14 directly or through one or more other components, such as the estimator 16. The processor 18 and the beamformer 14 are within a same housing, on a same circuit board, share a same power source or are otherwise integrated within the system 10.

The processor 18 is operable to automatically detect a region of interest for further computations or alterations. For example, an algorithm is applied to identify a region of interest in data for a two or three dimensional image or as a function of space and/or time in the M-mode data.

The processor 18 is operable to automatically compute a pressure gradient as a function of ultrasound data, such as ultrasound data representing spatial locations within a region of interest. Since the processor 18 is part of the system 10, the pressure gradient is computed as the ultrasound data is generated or in real-time. Alternatively, the pressure gradient is computed from locally or remotely stored ultrasound data by the processor 18 within the system 10 or by a different processor.

The display 20 is a CRT, LCD, plasma, projector, touch screen or other now known or later developed display. The display 20 receives ultrasound data in a display format from the processor 18, the estimator 16 or other component. For example, the display 20 displays a B-mode image overlaid with Doppler velocity information in a region of interest and with textual or graphic data. A color M-mode display based on a line extending through the region of interest is also displayed. As another example, in a separate display or adjacent to the display in the example above, an image of the pressure gradients within the region of interest on the B-mode overlay or on a region of interest in the color M-mode image is displayed. The image of pressure gradients is a parametric image, providing pressure gradients for different spatial locations and/or different times. Alternatively, the pressure gradients are displayed as a graph, chart or text.

Using the ultrasound system 10 or a different system, pressure gradient is measured with ultrasound. A patient is scanned, such as scanning with acoustic energy in a one, two or three dimensional region. The scanning sequence is for acquiring velocity information. The velocity information is for color M-mode or Color Doppler (velocities for each spatial location in a two or three dimensional region). For example, a 5 MHz multiple plane transesophageal echo transducer is used. From a midesophageal imaging window, a basal four-chamber view is obtained. An M-mode cursor is aligned across the mitral valve in parallel with LV inflow using two-dimensional color Doppler flow mapping. The color Doppler velocities are obtained using the M-mode format, providing the spatio-temporal velocity distribution along the Doppler scan line from the LA to the LV throughout the cardiac cycle. The spatial resolution is approximately 0.5 mm, the temporal resolution is 5 ms, the pulse repetition frequency is 5-7.5 KHz, and the velocity resolution is 6.25% of the Nyquist velocity (typically about 3 cm/s). Inclusion of the inertial term in the noninvasive pressure difference calculation significantly increased the temporal correlation with catheter-based measurement.

Figure 2:
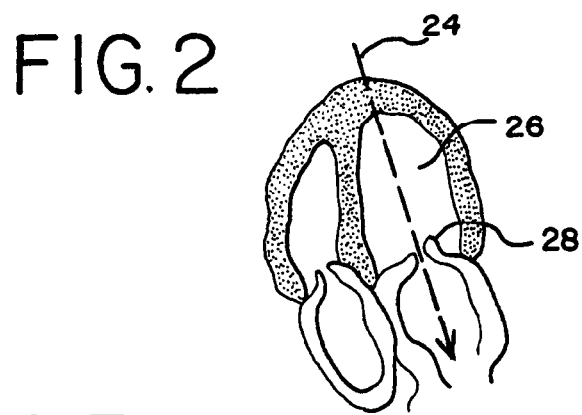
FIG. 2 is a graphical representation of scan line positioning of one embodiment for measurement of pressure gradient.

While pressure gradient may be determined for any location, the velocity information is for blood flow within the heart in one embodiment. FIG. 2 shows a scan line 24 positioned through the major axis of the left ventricle 26 and mitral valve 28 of an ultrasound apical 4 chamber view (A4C) of a heart. Pulsed wave Doppler measurements are made for fluids through the mitral valve. The Doppler cursor or scan line 24 is in parallel with the streamline of the inflow and is positioned in the midline streamline of the inflow tract. The inflow from the left atrium to the left ventricle is assumed to form a streamline. Flow turbulence might blow away the streamline assumption for a pathological valve. Other alignments may cause an error. The alignment shown in FIG. 2 allows measuring meant of the pressure gradient during early rapid filling. Early rapid filling is the process of how the blood fills the ventricle. Diastolic filling starts with the onset of mitral valve opening and continues until mitral valve closure. E-wave velocity is the peak velocity of this early filling and the desired information to identify the peak pressure gradient.

Figure 3:
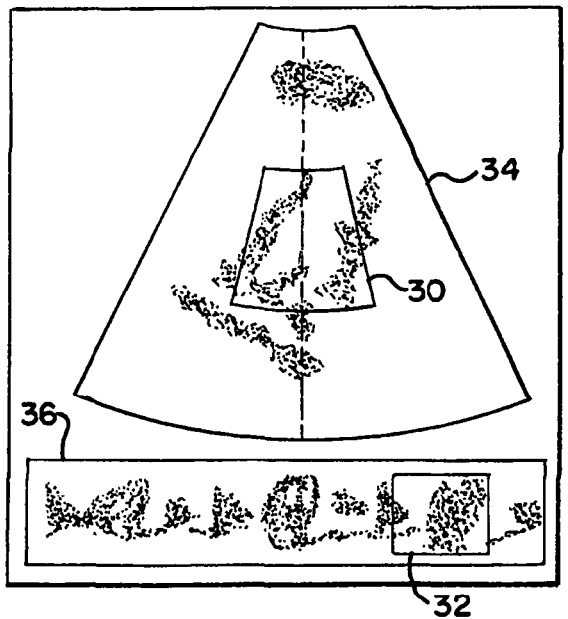
FIG. 3 is a graphical representation of one embodiment of regions of interest in two dimensional and color M-mode images.

The pressure gradient is calculated for an entire scanned region. Alternatively, the pressure gradient is calculated for a region of interest as shown in FIG. 3. The region of interest 30, 32 is automatically detected in a one, two or three dimensional image (34, 36). For example, the region of interest 32 is automatically detected from M-mode data 36. The beginning and ending times for the region of interest 32 in the M-mode data are detected as a function of an occurrence of an R-wave, such as bounding diastole phase (e.g., early filling and the left atrium contraction) of the heart cycle. The top and bottoms of the region of interest 32 are set a priori or detected based on a velocity border in the color M-mode data. Boundary detection, thresholding, triggering and/or other processes may be used to determine a region of interest.

The region is automatically detected in response to a user trigger, such as depressing a button or selecting a type of imaging. Alternatively, the region of interest is at least in part or entirely identified by a user, such as through selection of points, positioning a geometric shape or tracing a boundary. In yet another alternative embodiment, no region of interest is identified.

A pressure gradient is computed automatically as a function of ultrasound data responsive to the scanning. The pressure gradient is computed with the ultrasound system 10 or other system in real time with the scanning. The computations are performed as the ultrasound data is acquired and without transfer to a different platform than the ultrasound system.

The pressure gradient is computed for each spatial location within an image or region of interest. The pressure gradient is computed for each spatial location within a one, two or three dimensional region. For example, the pressure gradient is computed for a two dimensional region of interest as a function of velocity data representing the region at a given time or at different times. As another example, the pressure gradient is computed as a function of velocity data along the scan line at a plurality of different times for color M-mode data. Alternatively, the pressure gradient is computed for each of one or more regions, such as determining a single pressure gradient for color M-mode data as a function of time.

The velocity estimates have no or little aliasing. For example, a user adjusts the pulse repetition frequency or other characteristic to avoid or limit aliasing. As another example, an automated process adjusts a characteristic, such as pulse repetition frequency, to avoid or limit aliasing. As yet another example, an anti-aliasing filter filters the velocity data to remove or reduce aliased information. In one embodiment, color M-mode data at each depth is filtered as a function of time. The anti-aliasing filer is applied across each horizontal line in the region of interest or the color M-mode image (i.e., for each spatial point (depth) along the beam, the data is dealiased in time). The anti-aliasing filtering may include modeling velocity as a function of time and identifying velocities with a smallest error from the modeled velocity as discussed below, low pass spatial or temporal filtering or other now known or later developed anti-alias filtering.

In addition or as an alternative to anti-aliasing, spatial and/or temporal filtering is applied to the velocity data. For example, a spatial-temporal low pass filter is applied to the color M-mode data. Any now known or later developed filtering may be used, such as a 2-D spline to smooth data. Other processing of the velocity information may be provided.

The pressure gradient is computed from the velocity information. The pressure gradient is computed using Euler's equation, the Navier-Stokes' equation or other process. The density $\rho$ for incompressible fluid is a constant. When pressure, p, is the only force that acts on a fluid element, a motion equation of the fluid element can be derived by applying the conservation argument to momentum flux. The rate of the momentum change may be denoted as $$\rho \frac{D\vec{u}}{Dt},$$

where $\vec{u}$ is velocity and t is time. According to Newton's law, the momentum change must equal the applied forces. The Euler equation of motion for this ideal fluid is:

$$\rho \frac{D\vec{u}}{Dt} = \rho \left( \frac{\partial \vec{u}}{\partial t} + \vec{u} \cdot \nabla \vec{u} \right) = -\nabla p \quad (1)$$

When internal friction (viscosity) and gravity forces are considered, equation (1) becomes:

$$\rho \frac{D\vec{u}}{Dt} = \rho \left( \frac{\partial \vec{u}}{\partial t} + \vec{u} \cdot \nabla \vec{u} \right) = -\nabla p + \mu \nabla^2 \vec{u} + \rho \nabla G \quad (2)$$

which is the Navier-Stoke equation. Using Euler's equation (1), the definition of the total derivative is:

$$\rho \frac{D\vec{u}}{Dt} = \rho \left( \frac{\partial \vec{u}}{\partial t} + \vec{u} \cdot \nabla \vec{u} \right)$$

Leaving the right hand side of equation (1):

$$\rho \left( \frac{\partial \vec{u}}{\partial t} + \vec{u} \cdot \nabla \vec{u} \right) = -\nabla p$$

Where the velocity is one dimensional, such as only representing gradient information along the scan line, nominally the z-direction, the equation above simplifies to:

$$\rho \left( \frac{\partial u}{\partial t} + u \frac{\partial u}{\partial z} \right) = -\frac{\partial p}{\partial z}$$

Ultrasound velocity may include two or three dimensional vector values. When the velocity direction is along streamline of the flow, the pressure gradient in equation (1) is rewritten as, $$\frac{\partial p}{\partial s} = -\rho \left( u \frac{\partial u}{\partial s} + \frac{\partial u}{\partial t} \right) = -\rho u \frac{\partial u}{\partial s} - \rho \frac{\partial u}{\partial t}$$

where s is the spatial notation (along the streamline), and t is the time notation. The first term on the right side, $$-\rho u \frac{\partial u}{\partial s},$$

a convective term, and the second term, $$-\rho \frac{\partial u}{\partial t},$$

is an inertial term.

The pressure gradient is estimated using $$\rho\left(\frac{\partial u}{\partial t} + u\frac{\partial u}{\partial z}\right).$$

For example, a derivative of velocity as a function of time is determined for each spatial location. The velocity is multiplied by a derivative of velocity as a function of distance along a scan line. A sum of the temporal velocity derivative and the velocity multiplied spatial derivative of velocity is multiplied a density constant. The result is the pressure gradient. The pressure gradient is computed for each spatial location from the corresponding velocity values. Other calculations may be used.

For calculating the temporal derivative, the elemental time increment is one time sample (e.g., each time sample corresponding to a column for color M-mode data or an image in a sequence of images for two or three dimensional pulsed wave Doppler data). The elemental spatial sample is the sampling rate of the color output of the beam (e.g., the range gate sampling distance and/or the scan line or scan converted pixel lateral distance). Calculation of the derivatives results in no derivative data for one row (first or last) and one column (first or last) of the color M-mode or color Doppler data. Of course, higher order estimates of the partial derivatives may be made with the consequence of additional lost rows or columns.

Figure 4:
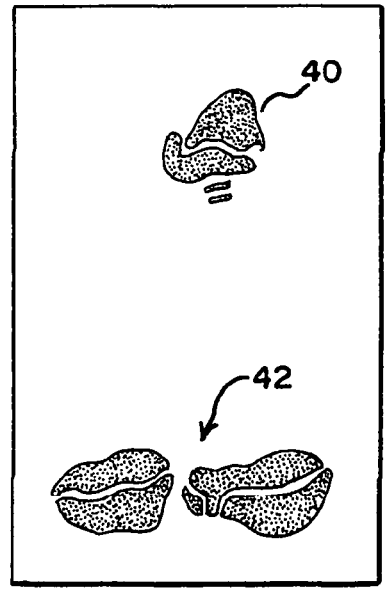
FIG. 4 is a graphical representation of a pressure gradient display in one embodiment for the regions of interest of FIG. 3.

The pressure gradient is displayed, such as text, graph or an image. As an image, the pressure gradient is displayed as a parameter modulating a display value within the two or three dimensional region of interest. FIG. 4 shows a first image 40 of the pressure gradient within the region of interest 30 of the image 34 of FIG. 3. FIG. 4 also shows an alternative or additional second image 42 of the pressure gradient for a portion of the image 36 of FIG. 3. One half of the pressure gradient image 42 corresponds to the region of interest 32. The pressure gradient image 42 is alternatively only for the region of interest 32 or for the entire image 36. The pressure gradient of each pixel modulates the intensity or gray scale of the pressure gradient image 40. Color, brightness or other modulation may be used.

Flow Estimation

Flow information is determined with ultrasound. The velocity of the tissue or fluid motion, $\vec{v}(t)$, is mathematically modeled by a second order polynomial or other function and the model parameters are estimated based upon least squared method. Higher order polynomial models may be used or, for periodic pulsatile velocities, periodic trigonometric functional models may be used.

Figure 5:
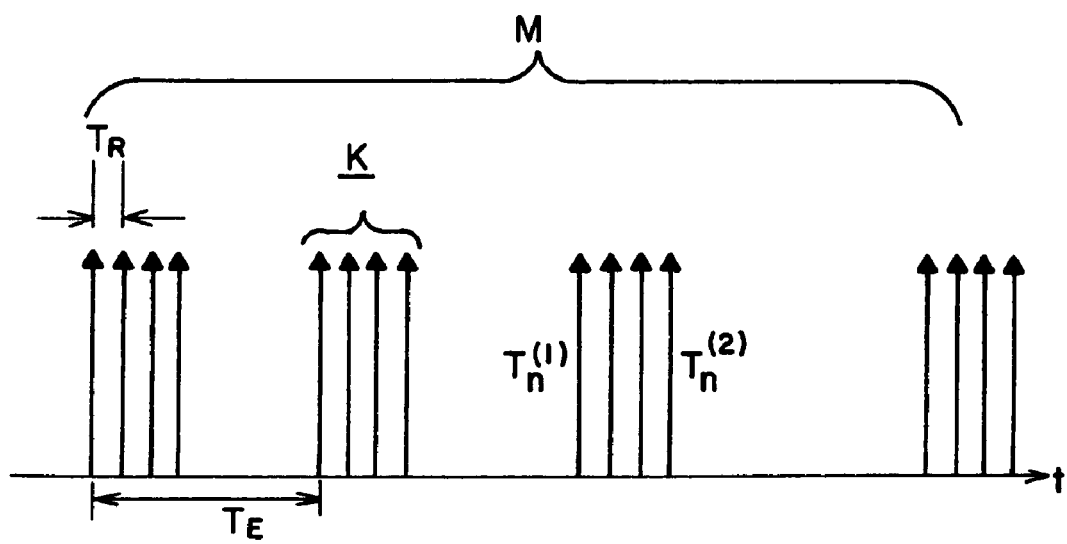
FIG. 5 is a graphical representation of one embodiment of a sequence of pulses for estimating velocity.

Small ensemble sizes and improved persistence performance may be provided based on estimation through modeling. Ultrasound information is acquired with a fewer number of pulses or pulses over a longer time period than for Doppler correlation. FIG. 5 shows transmitting a sequence of M ensembles or elements, such as at least two, of K pulses, such as five or fewer pulses. K is the number of pulses in each element pulse group or the ensemble size. More or fewer number K of pulses in each ensemble or number of ensembles in the sequence may be used. $T_R$ is the pulse repetition interval which is the same or different for each ensemble K or even within a given ensemble K. $T_E$ is the frame repetition interval. The pulses of each ensemble are fired in a uniform (or non-uniform) distribution of time interval denoted as $T_E$. $T_E$ is related the frame rate, and $T_R$ is related to the maximum velocity observed and is the inverse of the PRF. A time between a last pulse of a first of one ensemble and a first pulse of a second, temporally adjacent, sequential ensemble is at least four times a pulse repetition interval of the first ensemble. Other relationships, such as at the pulse repetition interval, may be used. $T_n^{(1)}$ is the time for the first pulse of nth element, and $T_n^{(2)}$ is the time for the last pulse of nth element. Any of the parameters discussed above may be the same or vary for each pulse, ensemble or sequence.

The pulses are used to estimate velocity. Velocity estimates for color flow detection, color M-mode, tissue imaging, or other modes are provided. Vessel wall and myocardium analysis may use the sequence of pulses since the acceleration of the flow and tissue can be computed directly from the results provided from the method.

Each pulse corresponds to a focused transmission and reception along a given scan line. Alternatively, each pulse corresponds to a plane wave transmission and reception using focused beams or Fourier analysis. Plane wave transmissions allow for more rapid scanning of a region, such as for real time three dimensional images. Transmitting a plurality of plane waves for velocity estimation may reduce frame rate undesirably. By estimating from a fewer number of pulses and/or pulses associated with different velocities or transmitted over a longer time period, frame rate reduction may be lessened.

The sequence of pulses is used to estimate velocity and acceleration simultaneously by modeling and/or least squares analysis. At the time when the nth ensemble is fired, the velocity at the first pulse is:

$$v(T_n^{(1)}) = \vec{a}_0 + nT_E\vec{a}_1 + (nT_E)^2\vec{a}_2 \qquad (3)$$

Figure 6:
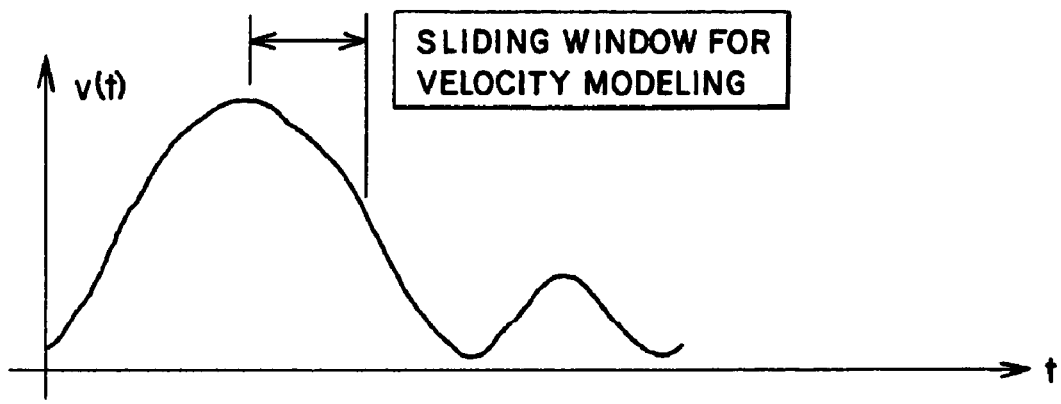
FIG. 6 is a graphical representation of one embodiment of a model of velocity as a function of time.

The velocity may be determined over a time period associated with different velocities for a given spatial location. By observing the profile of the blood velocity in the time domain as shown in FIG. 6, $\vec{v}(t)$ is approximated or modeled by a second order polynomial or other function. For example, the second order polynomial:

$$\vec{v}(t) = \vec{a}_0 + (t-T_0)\vec{a}_1 + (t-T_0)^2\vec{a}_2 \qquad (4)$$

is used, where $T_0$ is the start time point in time, t. The modeling of the velocity is within the sliding window shown in FIG. 6. Each window is associated with a sequence of pulses. Different sequences may or may not overlap with other sequences, such as the moving window corresponding to dropping an earliest ensemble from a previous sequence and adding a most recent ensemble not in the previous sequence.

The velocity and acceleration terms are solved by identifying a least squares fit of the ultrasound information to the model, such as the polynomial equation (4). The polynomial includes both velocity and acceleration terms. The form of the equation (3) indicates that the velocity at time $T_0$ is $\vec{a}_0$. A least squared method is used to estimate the parameters $\{\vec{a}_0, \vec{a}_1, \vec{a}_2\}$. Rewriting equation (3) in the form of equation (4) based on the pulse numbers rather than time provides:

$$v(n) = a_0 + B(n)a_1 + C(n)a_2 \quad (5)$$

where, $$v(n) = \frac{\Delta\varphi}{A} \quad (6a, 6b, 6c)$$

$$A = \frac{2\omega(K-1)T_R\cos(\theta)}{c},$$

$$B(n) = nT_E + \frac{1}{2}(K-1)T_R,$$

$$C(n) = n^2 T_E^2 + nT_E(K-1)T_R + \frac{1}{3}(K-1)^2 T_R^2.$$

In the pulse sequence, groups of pairs of pulses are fired. The phase change for each individual pair may be computed, so $\Delta\phi(n)$, n=0, 1, M−1, is known. Therefore, v(n) is also known.

A least squared method is used to estimate the parameters $\{a_0, a_1, a_2\}$. The sum of square error is:

$$e^2 = \sum_{n=0}^{M-1} (v(n) - a_0 - B(n)a_1 - C(n)a_2)^2 \quad (7)$$

Based on calculus operations, the parameters are:

$$\begin{pmatrix} a_0 \\ a_1 \\ a_2 \end{pmatrix} = \begin{pmatrix} w_{11} & w_{12} & w_{13} \\ w_{21} & w_{21} & w_{23} \\ w_{31} & w_{32} & w_{33} \end{pmatrix} \begin{pmatrix} E[v] \\ E[vB] \\ E[vC] \end{pmatrix} \quad (8)$$

where, $$E[v] = \frac{1}{M} \sum_{n=0}^{M-1} v(n), \quad (9a, 9b, 9c)$$

$$E[vB] = \frac{1}{M} \sum_{n=0}^{M-1} v(n)B(n),$$

$$E[vC] = \frac{1}{M} \sum_{n=0}^{M-1} v(n)C(n).$$

W is only the function of $T_E$, $T_R$, and M, so can be predetermined in real time application. Using E[ ] to denote the moment for the product of variables B and C provides, for instance:

$$E[BC] = \frac{1}{M} \sum_{n}^{M-1} B(n)C(n) \quad (10)$$

where u is defined as:

$$u = E^2[BC] + E[B^2]E^2[C] + E^2[B]E[C^2] - 2E[BC]E[B]E[C] - E[B^2]E[C^2]$$

The elements of the coefficient matrix in equation (8) are:

$$w_{11} = \frac{E^2[BC] - E[B^2]E[C^2]}{u}, \quad w_{12} = \frac{E[B]E[C^2] - E[BC]E[C]}{u},$$

$$w_{13} = \frac{E[B^2]E[C] - E[BC]E[B]}{u}, \quad w_{21} = \frac{E[B]E[C^2] - E[BC]E[C]}{u},$$

$$w_{22} = \frac{E^2[C] - E[C^2]}{u}, \quad w_{23} = \frac{E[BC] - E[B]E[C]}{u},$$

$$w_{31} = \frac{E[B^2]E[C] - E[BC]E[B]}{u}, \quad w_{32} = \frac{E[BC] - E[B]E[C]}{u},$$

$$w_{33} = \frac{E^2[B] - E[B^2]}{u}.$$

The parameters $\{a_0, a_1, a_2\}$ are calculated from equations (8) and (9). Solving the matrix based on the least squares analysis provides simultaneous computation of both the velocity $a_0$ and the acceleration $a_1$. The computation is linear and is comparable to exiting autocorrelation estimation in computational complexity. The storage memory in the estimator 16 of the data is M times the storage required estimating from autocorrelation because either the baseband signal for each pair data or $\Delta\phi$ is used for the least squared computation in M consecutive groups.

Modeling over multiple ensembles allows for a small ensemble size to achieve the same estimation performance as large ensemble size using autocorrelation or Doppler processing, resulting in frame rate improvement. Since fewer pulses are fired between a relatively large time interval ($T_E$), the power of the color detection pulse may be increased to achieve better sensitivity and penetration. Since the results are based on curve fitting for a group of elements in the time domain, conceptually, the curve fitting may give a better result than conventional persistence.

The modeling with least squares fitting may also be used to limit aliasing. Aliasing occurs when improper PRF is used. In phase representation, aliasing results in phase jump in the amount of $2\pi$. In the modeling estimation, aliasing data points are detected by using outlier detection and may be corrected efficiently, improving the detection accuracy of both velocity and acceleration.

In a first method, a set of phase points, v(n), n=0, 1, 2, ... M−1, are given by solving equation (7). The error $e^2$ is the metrics of the fitness of the model with the given data. A bad fitness occurs when the data are noisy or when aliasing occurs (outliers). An iterative method identifies the aliasing. The data points v(n), n=1, 2, 3, . . . , M−1 are input. Equation (7) is solved to obtain an initial $e_0^2$. One or more given data points v(k) are assumed to be aliased. The assumption may be made for every point or only points more likely to be aliased, such as based on large variation between adjacent data values. The aliasing is corrected. Equation (7) is solved again to provide a new $e_n^2$. The assumption of aliasing is accepted, the data altered accordingly and the error $e_0^2$ updated, if $e_0^2 > e_n^2$. Otherwise, the assumed aliased data points are considered not to be aliased. The process repeats for subsequent error calculations based on assuming other data points are aliased. The process repeats to identify a minimum $e_0^2$ or until a threshold number of iterations or error is obtained. The above method is an exhaustive search method. Other outlier detection methods may be adopted to modify the above algorithm.

In a second method, the given data points are assumed to not contain any aliasing. These data points are used to predict whether the next data point is aliased. Based on the model, the next data point can be predicted, and the comparison between the predicted data and the input data indicate any aliasing. For example, the predicted value $\hat{v}(n+1)$ is computed with the model based on the data points v(0), v(1), v(2), . . . , v(M−1). Given the detected value v(n+1), the min {|v(n+1)−$\hat{v}$(n+1)|, $|v(n+1)-\hat{v}(n+1)+2\pi|, |v(n+1)-\hat{v}(n+1)-2\pi|\}$ is calculated. Once the aliasing is detected and corrected, the model parameter is estimated based on the data points v(1), v(2), v(3), ... , v(M), and so on.

A combination of both methods may be used for anti-aliasing. For example, the first method is used either at the beginning or periodically, and the second method is used after the first method is applied to the data v(0), v(1), v(2), ... , v(M−1).

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for measuring pressure gradient with ultrasound, the method comprising:
   scanning multiple spatial locations with an ultrasound system, the spatial locations being fluid locations;
   automatically computing, with the ultrasound system in real time with the scanning, pressure gradients as a function of ultrasound data responsive to the scanning of the multiple spatial locations;
   wherein scanning comprises scanning a two or three dimensional region with ultrasound for velocity information, and wherein automatically computing as a function of the ultrasound data comprises computing the pressure gradients, for spatial locations distributed in two or three dimensions, as a function of velocity data representing the two or three dimensional region at a given time;
   displaying an image of pressure gradients distributed over all the two or three dimensions within the two or three dimensional region;
   applying an anti-aliasing filter for each depth as a function of time to the ultrasound data; and
   applying a spatial-temporal filter to the ultrasound data.

2. The method of claim 1 wherein automatically computing with the ultrasound system in real time with the scanning comprises computing the pressure gradient as the ultrasound data is acquired and without transfer to a different platform than the ultrasound system.

3. The method of claim 1 wherein scanning comprises scanning along a scan line passing through a mitral valve.

4. The method of claim 1 wherein automatically computing comprises:
   (a) computing the derivative of velocity as a function of time;
   (b) computing the derivative of the velocity as a function of space as velocity multiplied by a derivative of velocity as a function of distance along a scan line; and
   multiplying a density constant with a sum of (a) and (b).

5. The method of claim 1 wherein applying the anti-aliasing filter comprises:
   modeling velocity as a function of time;
   identifying velocities with a smallest error from the modeled velocity.

6. An ultrasound system for measuring pressure gradient with ultrasound, the system comprising:
   a beamformer for generating ultrasound data representing a plurality of spatial locations, the spatial locations being fluid locations;
   a processor connected with the beamformer for automatically computing, as ultrasound data is generated, a pressure gradient as a function of the ultrasound data representing the plurality of spatial locations; and
   wherein the processor is operable to compute the pressure gradient for each spatial location within a spatial two or three dimensional region of interest;
   further comprising a display operable to display an image of the pressure gradients within the spatial two or three dimensional region of interest;
   wherein the ultrasound data further comprises color M-mode data;
   an anti-aliasing filter for filtering the color M-mode data at each depth as a function of time, the filtering comprising:
   modeling velocity as a function of time; and
   identifying velocities with a smallest error from the modeled velocity.

7. The ultrasound system of claim 6 wherein the ultrasound data further comprises M-mode data, and wherein the processor is operable to automatically detect a region of interest in the M-mode data, the automatic computing being for the ultrasound data only within the region of interest.

8. The ultrasound system of claim 6 wherein the ultrasound data comprises velocity data, and wherein the processor is operable to:
   (a) compute a derivative of velocity as a function of time;
   (b) compute velocity multiplied by a derivative of velocity as a function of distance along a scan line; and
   multiplying a density constant with a sum of (a) and (b), a result being the pressure gradient.

9. A method for determining flow information with ultrasound, the method comprising:
   acquiring ultrasound information; and
   simultaneously determining velocity and acceleration for a spatial location from the ultrasound information, the acceleration being a function of time, and simultaneously comprising solving for the velocity and acceleration as outputs from a same equation at a same time, wherein simultaneously determining velocity and acceleration comprises modeling velocity as a polynomial with an acceleration term and estimating parameters of the model based on solving a matrix, the parameters including the acceleration term and a velocity term.

10. The method of claim 9 wherein determining the velocity comprises determining the velocity from ultrasound information acquired over a time period associated with different velocities.

11. The method of claim 10 wherein acquiring the ultrasound information comprises transmitting a sequence of at least two ensembles of five or fewer pulses in a respective at least two frame repetition intervals, and wherein determining velocity comprises determining velocity as a function of the sequence.

12. The method of claim 11 wherein a time between a last pulse of a first of the at least two ensembles and a first pulse of a second of the at least two ensembles is at least four times a pulse repetition interval of the first ensemble, the first and second ensembles being adjacent ensembles sequentially.

13. The method of claim 10 wherein acquiring ultrasound information comprises acquiring in response to plane wave transmissions.

14. The method of claim 9 wherein simultaneously determining velocity and acceleration comprises identifying a least squares fit of the ultrasound information to a model.

15. The method of claim 9 wherein simultaneously determining velocity and acceleration comprises the modeling of velocity as a second order polynomial and estimating the parameters of the model based on a least squares calculation.

16. The method of claim 9 further comprising:
limiting aliasing as a function of velocities corresponding to a least error.

17. A method for de-aliasing ultrasound velocity information, the method comprising:
acquiring velocity information;
fitting velocity information to a model;
computing an error of a velocity fit to the model;
recomputing the error of the velocity fit to the model based on one or more velocity data replaced by an alias equivalent; and
choosing an unaliased velocity data associated with the minimum error of the velocity fit to the model.

* * * * *